United States Patent [19]

Sitko et al.

[11] Patent Number: 5,152,286
[45] Date of Patent: Oct. 6, 1992

[54] METHOD OF MICROWAVE RESONANCE THERAPY AND DEVICE THEREFOR

[75] Inventors: Sergei P. Sitko; Valery E. Lobarev; Nikolai D. Kolbun, all of Kiev, U.S.S.R.

[73] Assignee: Mezhotraslevoi Nauchnoinzhenerny Tsentr "Vidguk", Kiev, U.S.S.R.

[21] Appl. No.: 762,084

[22] Filed: Sep. 19, 1991

Related U.S. Application Data

[63] Continuation of Ser. No. 348,954, May 8, 1989, abandoned.

[51] Int. Cl.$^5$ ............................................. A61N 5/02
[52] U.S. Cl. ..................................... 128/422; 128/804
[58] Field of Search ........................ 128/804, 422, 907

[56] References Cited

FOREIGN PATENT DOCUMENTS

| | | | |
|---|---|---|---|
| 3721271 | 1/1988 | Fed. Rep. of Germany | 128/804 |
| 1341762 | 1/1987 | U.S.S.R. | |
| 1442221 | 12/1988 | U.S.S.R. | 128/804 |
| 2171309 | 8/1986 | United Kingdom | 128/804 |

OTHER PUBLICATIONS

Elektronnaya promyshlennost, 1 (159), 1987, A. N. Balaba et al: "Apparaty dlya mikrovolnovoi reflexodiagnostiki i terapii Elektronika-KVCh", p. 30.

*Primary Examiner*—Lee S. Cohen
*Attorney, Agent, or Firm*—Fleit, Jacobson, Cohn, Price, Holman & Stern

[57] ABSTRACT

The method consists in affecting a biologically active zone characteristic of pathology treatment with low-intensity EHF electromagnetic radiation—representing continuous spectrum oscillations in a therapeutically effective frequency region at a spectral power density from $10^{-6}$ W/Hz to a value approaching a quantum limit with the duration of a single treatment procedure being within half an hour. The course of treatment includes 1 to 15 procedures. The device for accomplishing the proposed method comprises an electromagnetic EHF oscillation source made up as a noise generator having its output connected with a radiating antenna.

9 Claims, 1 Drawing Sheet

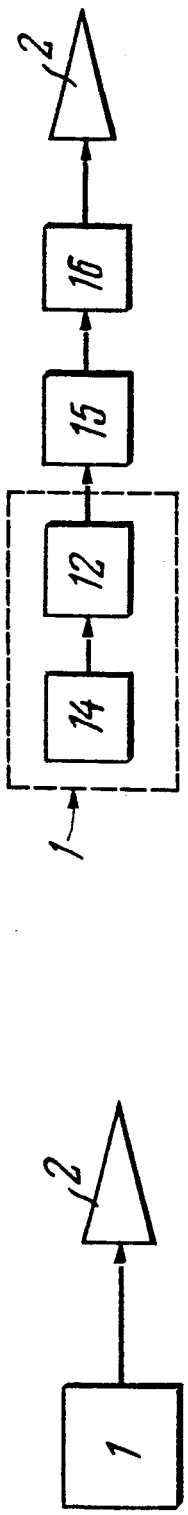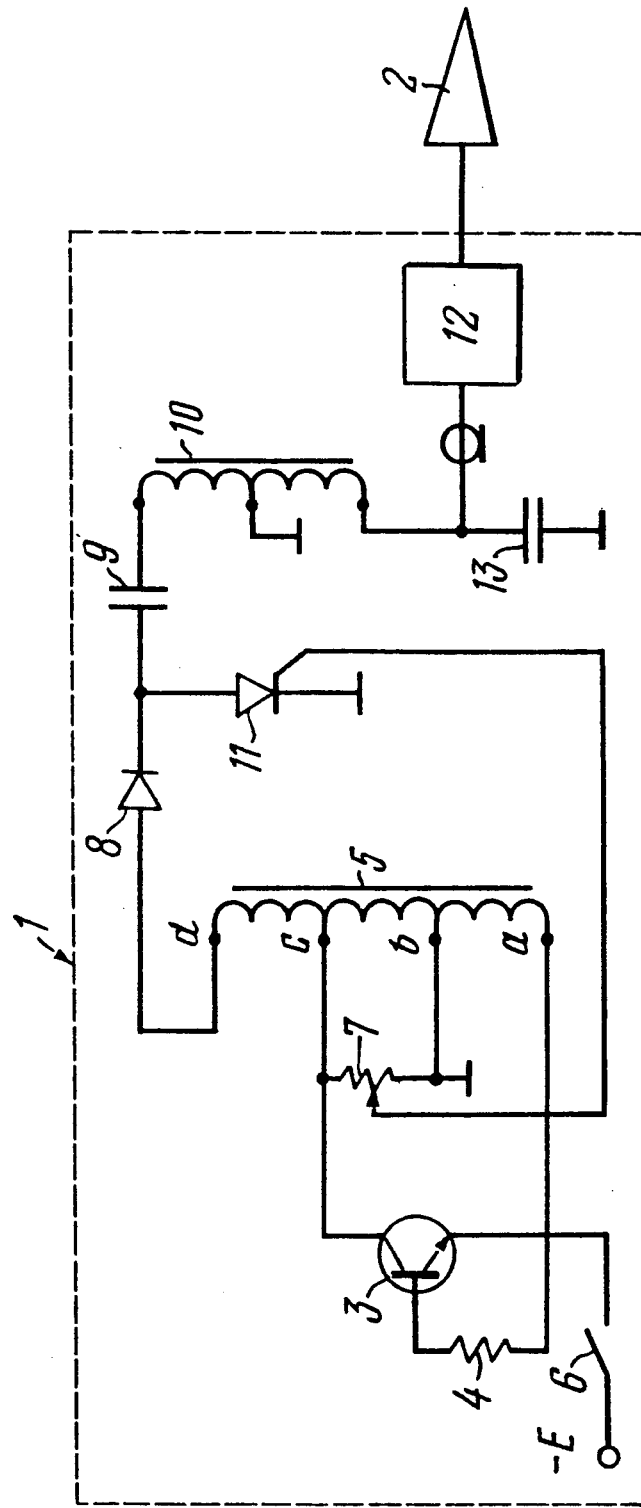

ns of application Ser. No. 07/348,954, filed May 8, 1989, now abandoned.

METHOD OF MICROWAVE RESONANCE THERAPY AND DEVICE THEREFOR

This application is a continuation of application Ser. No. 07/348,954, filed May 8, 1989, now abandoned.

FIELD OF THE INVENTION

The present invention relates to the treatment of disability or disease by affecting in a non-contact manner biologically active zones with electromagnetic microwave fields, more particularly, to a method of microwave resonance therapy and a device therefor.

The invention can be used to best advantage for the treatment of patients suffering from etiologically different ailments such, for example, as disorders of the gastroduodenal, emotional and motivational spheres, locomotor system disturbances, chronic pulmonary diseases, narcomania, certain oncologic maladies, infantile cerebral paralysis and the like.

BACKGROUND ART

It has been recently ascertained that the action of low-intensity (nonthermal) radiation at certain fixed frequencies in the millimetric wave band (EHF radiation) makes it generally easier to overcome functional derangement of the organism and prepare it for resisting the toxic effect of chemical substances and ionizing radiation. The action of EHF radiation on the organism causes its cells to produce signals enabling recovery or adaptation to suit changing environmental conditions. If generation of such signals is disrupted or hindered due to age or earlier ailments, their deficiency may be compensated by deriving similar signals from external sources. The utilization of electromagnetic low-intensity EHF radiation within 10 mW/cm$^2$ has been particularly effective in medical and biological investigations and in the treatment of certain maladies.

There is known a method of microwave resonance therapy (cf. SU, A, 1,341,762), in which acupuncture zones of the organism are affected with electromagnetic low-power EHF radiation with a power density of 0.01 to 10 mW/cm$^2$ at a fixed individually chosen frequency in the range of 44 to 70 GHz. At the initial stage, the oscillation frequency is continuously varied in the aforesaid range until a steady sensory response is obtained in the zone exposed to radiation. Thereafter the treatment is continued with the above parameters essentially unchanged until the sensory response is no longer detected in the zone exposed to radiation.

A major disadvantage of the known method is that a period of 2 to 4 hours or even longer is needed to select a fixed frequency individually, which appreciably increases the treatment time and the energy level in affecting the organism with electromagnetic radiation.

Moreover, frequency selection based on a complex of patient's sensations is influenced by subjective factors.

There is also known a device for microwave resonance therapy (cf. Elektronnaya promyshlennost, 1 (159), 1987, A. N. Balaba et al: "Apparaty dlya mikrovolnovoi reflexodiagnostiki i terapii" "Elektronika-KVCh", p. 30) comprising an electromagnetic EHF oscillation source whose output is connected with a radiating antenna. The electromagnetic oscillation source is essentially a generator provided with an electrically controlled attenuator which, in conjunction with a detecting means, makes it possible to continuously adjust and stabilize the emissive output power level and to effect continuous generation and amplitude modulation separately or jointly with frequency modulation.

The disclosed device has basically the same disadvantages as the afore-mentioned prior art method.

SUMMARY OF THE INVENTION

It is an object of the present invention to create a method of microwave resonance therapy providing for a shorter treatment period and a smaller overall absorbed radiation dose.

Another object of the invention is to save time and labour in treatment procedures.

A further object of the invention is to enhance the therapeutical effect on patients suffering from chronic pulmonary diseases, locomotor system disturbances, infantile cerebral paralysis, disorders of the gastroduodenal, emotional and motivational spheres, etc.

An additional object of the invention is to increase safety in affecting the patient with electromagnetic radiation.

A still further object of the invention is to enhance effectiveness of the proposed method so that the patient may be suitably affected with electromagnetic radiation at all therapeutically effective frequencies.

Still another object of the invention is to create a method of microwave resonance therapy, which would exclude the search for and individual selection of electromagnetic radiation components having resonant therapeutically effective frequencies, which are optimal for each patient.

One more object of the invention is to create a device for microwave resonance therapy whose utilization would save time and labour in the treatment of patients and ensure a drastic decrease in the energy level of electromagnetic radiation with a view to reducing an overall absorbed dose and increasing safety in the course of treatment.

The foregoing and other objects of the invention are attained by that in a method of microwave resonance therapy consisting in affecting biologically active zones characteristic of pathology treatment with low-intensity electromagnetic EHF radiation, according to the invention, an electromagnetic field is set up by continuous spectrum oscillations in a therapeutically effective frequency region at a spectral power density from $10^{-6}$ W/Hz to a value approaching a quantum limit, the duration of a single treatment procedure being within half an hour, while the course of treatment includes 1 to 15 procedures as may be required.

In the preferred embodiment of the invention the spectral power density of electromagnetic radiation is in the range from $10^{-16}$ to $10^{-18}$ W/Hz.

It is advantageous that, in the treatment of patients suffering from uncomplicated duodenal ulcer, the biologically active zone E-36 of the body should be affected with electromagnetic radiation in the wave band from 1 to 10 mm at a spectral power density of $10^{-6}$ to $10^{-18}$ W/Hz with the duration of a single treatment procedure being within 25-30 min, the course of treatment including 7 to 15 procedures.

In one of the preferred embodiments of the invention, in the treatment of patients suffering from chronic nonspecific pulmonary ailments and the bronchoobstructive syndrome the biologically active acupuncture zones P-2 and G1-4 of the body are affected with electromagnetic radiation in the wave band from 1 to 10 mm at a spectral power density of $10^{-6}$ to $10^{-18}$ W/Hz with the duration of a single treatment action being within 20–30 min, the course of treatment including 8 to 14 procedures prescribed.

In another embodiment of the invention, in the treatment of patients suffering from postthyrotoxic encephal ophthalmopathy the biologically active acupuncture zones T-20, VB-1 and G1-4 of the body are affected with electromagnetic radiation in the wave band from 1 to 6 mm at a spectral power density of $10^{-6}$ to $10^{-18}$ W/Hz with the duration of a single treatment action being within 25–30 min, the course of treatment including 8 to 10 procedures mentioned above.

In still another embodiment of the invention, in the treatment of patients suffering from infantile cerebral paralysis the biologically active zones of the body are affected with electromagnetic radiation in the wave band from 1 to 6 mm at a spectral power density of $10^{-16}$ to $10^{-18}$ W/Hz with the duration of a single treatment action being up to 20 min, the course of treatment including up to 10 procedures prescribed.

In one more embodiment of the invention, in the treatment of patients suffering from chronic alcoholism, tabacism, manic-depressive psychosis and neuroses the biologically active points G1-4 and ZU-LI-PANG and the lung point on the floor of the auricle are affected with electromagnetic radiation in the wave band from 2 to 6 mm at a spectral power density of $10^{-16}$ to $10^{-18}$ W/Hz with the duration of a single treatment action being within 15–25 min, the course of treatment including 3 to 14 procedures described.

The foregoing and other objects of the invention are also accomplished by that in a device for microwave resonance therapy comprising an electromagnetic EHF oscillation source having its output connected with a radiating antenna, according to the invention, the electromagnetic oscillation source is a source producing continuous spectrum oscillations in a therapeutically effective frequency region at a spectral power density from $10^{-6}$ W/Hz to a value approaching a quantum limit.

It is preferable that the oscillation source used should have a spectral power density of electromagnetic radiation equaling $10^{-16}$ to $10^{-18}$ W/Hz.

In one of the preferred embodiments of the invention, the electromagnetic oscillation source is made as a noise generator.

In another embodiment of the invention, the noise generator comprises a supply voltage generating means connected to the input of an active element, and a means for channelling electromagnetic energy emitted by the active element, while the radiating antenna is connected with the output of said means for channelling electromagnetic energy.

In still another embodiment of the invention, said means for channelling electromagnetic energy is a waveguide adapted to act as a low-pass filter for electromagnetic radiation.

In one more embodiment of the invention, the proposed device additionally includes a waveguide transformer designed to interconnect said means for channelling electromagnetic energy and the radiating antenna.

The curative effect obtained through the utilization of the proposed method accomplished by the device for microwave resonance therapy according to the invention is characterized by a rapid action whereby the treatment period will be appreciably decreased as compared with conventional therapeutical techniques and with the prior art methods of microwave resonance therapy. Furthermore, stability of the therapeutical effect is substantially increased. Other advantages of the proposed method and the device therefor are an appreciably simplified treatment process and time- and labour-saving treatment procedures due to the fact that the need for selecting a desired resonant frequency is essentially eliminated.

For the above reasons, the treatment process according to the invention is regarded to be more effective inasmuch as the patient's organism can "select" from the radiation frequency spectrum those frequencies at which there occurs resonant interaction between the patient's organism and external electromagnetic radiation affecting biologically active zones. Under such conditions, the patient's organism will be an active element of the system for correcting its state.

The method and device forming the subject of the present invention make it possible to abandon chemotherapeutics and essentially exclude an adverse effect on the patient's organism, which has been confirmed by clinical tests.

Also, the method and the device in compliance with the invention are suitable for ambulatory and hospital use and for domiciliary aid, another advantage thereof being substantially reduced treatment expenses.

It should be noted that, in the treatment of patients suffering from infantile cerebral paralysis, the proposed method and the device therefor provide a greater therapeutical effect than the known facilities for drug, functional, physiotherapeutic, sanatorium, health resort and other kinds of treatment used for similar purposes.

An important advantage of the method and the device according to the invention is effecting treatment of pathology of the emotional and motivational sphere.

Another vital advantage of the proposed method and the device therefor is an unprecedentedly low energy level in the course of treatment (by six orders of magnitude lower than similar levels in the prior art facilities for microwave resonance therapy).

BRIEF DESCRIPTION OF DRAWINGS

These and other objects and features of the present invention will become more readily apparent from the detailed description of preferred embodiments thereof, taken in conjunction with the accompanying drawings wherein:

FIG. 1 is a block diagram of a device for microwave resonance therapy according to the invention:

FIG. 2 is a schematic circuit diagram of the device according to the invention; and FIG. 3 is a block diagram of a preferred embodiment of the device according to the invention.

DETAILED DESCRIPTION OF THE INVENTION

The proposed method of microwave resonance therapy essentially consists in the following. Biologically active zones of the patient's body (acupuncture points, hypersensitive or hyposensitive areas, Zakhariin-Head zones, scalp and plantar zones, etc.) associated with and characteristic of the treatment of specific pathology are affected with low-intensity EHF electromagnetic radiation representing continuous spectrum oscillations in a therapeutically effective frequency region. Besides, said electromagnetic radiation is characterized by a spectral power density from $10^{-6}$ W/Hz to a value approaching a quantum limit and equalling approximately $10^{-21}$ W/Hz.

The duration of one treatment procedure chosen within a 30-minute period depends on a variety of factors including individual susceptibility of the patient, stages and gravity of the disease, general physiological and hormonal conditions of the patient, type of pathology and so on.

With the above conditions taken into account, an important irradiation parameter is a mean-time spectral power density of electromagnetic radiation which is desirably maintained in the range from $10^{-16}$ to $10^{-18}$ W/Hz. Therapeutical practice shows that a curative effect is obtained in the course of treatment including 1 to 15 procedures. However, the treatment course should preferably involve 7 to 15 procedures.

Referring to the drawings the device for microwave resonance therapy according to the invention comprises an EHF noise generator (FIG. 1) designed to set up electromagnetic continuous spectrum oscillations and having its output connected with a radiating antenna 2 forming a directional electromagnetic radiation flux to irradiate the chosen biologically active zone on the patient's skin.

The generator 1 includes a supply voltage generating means using a blocking oscillator circuit and incorporating a transistor 3 (FIG. 2) and a resistor 4 in the base circuit of the transistor 3 connected to lead "a" of the winding of a pulse transformer 5 whose lead "c" is connected with the collector of the transistor 3. The emitter of the transistor 3 is connected with a negative terminal of a supply voltage source E through a switch 6. The collector of the transistor 3 is connected with a common bus and with lead "b" of the pulse transformer 5 through a variable resistor 7. Lead "d" of the pulse transformer 5 is connected with the anode of a diode 8 whose cathode is connected with a reservoir capacitor 9 inserted in series with the winding of a step-up autotransformer 10. A thyristor 11 acting as a gating element is connected via its anode to the cathode of the diode 8 and via its cathode to said common bus. The control electrode of the thyristor 11 is connected with a central lead of the resistor 7. The lead of the secondary winding of the autotransformer 10 is connected with a positive terminal of an active element 12 of the noise generator 1, which may be formed with a type 1MPAT diode, a semiconductor photodiode, a gaseous-discharge lamp, an avalanche transistor, a lambda diode, a tunnel diode or a backward diode. A filter capacitor 13 is chosen to suit a particular type of active element 12 used. The described construction of the device for microwave resonance therapy according to the invention provides at its output noise electromagnetic continuous-spectrum radiation in the wave band from 1 to 10 mm at a spectral power density from $10^{-6}$ W/Hz to a value approaching a quantum limit in the millimetric wave band.

In the preferred embodiment of the device illustrated in FIG. 3 the generator 1 comprises a supply voltage generating means 14 connected to the input of the active element 12. Connected to the output of the active element 12 is a means 15 for channelling electromagnetic energy emitted by the active element 12. The means 15 may comprise a hollow or dielectric waveguide, adapted to pass high frequencies of the electromagnetic radiation or a microstrip transmission line. The output of the means 15 is connected with the radiating antenna 2 by means of a waveguide transformer 16 designed to match wave impedances of the means 15 and the radiating antenna 2.

The device for microwave resonance therapy according to the invention operates in the following manner.

Inasmuch as electromagnetic radiation induced by the proposed device has a fairly low spectral power density, for example, $10^{-18}$ W/Hz, the noise generator 1 may be constructed in a simple manner. The device according to the invention may be operated from a low-power sourcce furnishing a voltage of about 2.5 to 5.5 V, which is increased by a voltage converter to a value required to provide for proper functioning of the active element 12 of the noise generator 1, for example, to 2 kV with the active element 12 built around a gaseous-discharge lamp or to 20 V in the case of a type 1MPAT diode.

Connecting the power supply E by the switch 6 to the emitter of the transistor 4 of the blocking oscillator causes the pulse transformer 5 to develop at its lead "d" positive voltage pulses having a great amplitude and a repetition rate equalling several kilohertz. Said pulses are fed through the diode 8 to charge the reservoir capacitor 9 to such a voltage level at the anode of the thyristor 11 when the next voltage pulse across the control electrode of the thyristor 11 derived from a voltage divider using the resistor 7 activates the thyristor 11. Thereafter the reservoir capacitor 9 is discharged through the thyristor 11 into the winding of the step-up autotransformer 10. During the discharging process, the secondary winding of the autotransformer 10 produces a high-voltage pulse fed to the active element 12 of the noise generator 1 setting up electromagnetic oscillations in the millimetric wave band. The established electromagnetic field is emitted outside through the radiating antenna 2. The discharge intervals of the reservoir capacitor 9 are controlled by the use of the variable resistor 7. The filter capacitor 13 is used to smooth out supply voltage ripple for the active element 12 of the noise generator 1.

To obtain a curvative effect, the antenna 2 should be brought as close as 5 to 20 mm to a biologically active zone of the patient's body, chosen for treatment of a specific type of pathology.

The proposed method and the device therefor will now be described further with reference to the following examples illustrating the treatment of specific types of pathology.

EXAMPLE 1

Treatment of Patients Suffering from Duodenal Ulcer

The proposed method was applied to a group of 94 male and female patients suffering from duodenal ulcer characterized by aggravation and the presence of Haude's niche. The age of the patients varied between 12 and 60 years. The illness period was in the range from 1 to 25 years.

The treatment process was as follows. Biologically active zones, that is, acupuncture points associated with a given type of pathology were affected with low-intensity electromagnetic radiation having a continuous spectrum in a therapeutically effective EHF region from 1 to 10 mm at a spectral power density of $10^{-6}$ to $10^{-18}$ W/Hz. It should be noted that a therapeutical effect was achieved even at smaller values of the spectral power density approaching a quantum limit (as low as $10^{-21}$ W/Hz).

The treatment carried out by the proposed device for microwave resonance therapy involved 7 to 15 procedures for each patient. Each daily procedure lasted for 25 to 30 minutes.

For example, patient A aged 45 was treated by the described method. Diagnosis: duodenal ulcer with a painful syndrome lasting for more than 14 years.

The painful periods because more frequent over the last 9 or 10 years. Then pain persisted and the condition did not change for 2 years preceding the experiment. The patient had been previously given a course of general therapeutic treatment, which did not, however, stop the painful syndrome. Objective investigation methods involving the use of roentgenoscopic and fibrogastroduodenoscopic facilities revealed the presence of the ulcerous defect on the bulb wall measured $0.8 \times 1.5$ cm$^2$. The prescribed course of treatment included 10 daily 25-minute procedures. During treatment, the patient had a sensation of pulsating heat in the abdominal cavity, accompanied by drowsiness and a message-like feeling in the abdominal cavity. The pain was relieved by the end of the prescribed course of treatment. Undesirable side-effects were not observed. A fibrogastroduodenoscopic analysis showed that the ulcer had cicatrized. No defects were revealed in the mucous membrane.

Effectiveness of treatment is illustrated by the following data confirmed by fibrogastroduodenoscopic investigation.

The ulcerous defect was completely healed in the case of 84 patients (89.4%) after a course of treatment including:

7 procedures for 8 patients;
8 procedures for 9 patients;
9 procedures for 17 patients;
10 procedures for 41 patients;
14 procedures for 2 patients;
15 procedures for 7 patients.

The ulcerous defect was healed by more than a half in the case of 9 patients (9.6%) after a course of treatment including:

10 procedures for 7 patients;
15 procedures for 2 patients.

A positive effect in curing the ulcerous defect was not observed with one patient (1%) of said group after 11 procedures.

EXAMPLE 2

Treatment of Patients Suffering from Chronic Nonspecific Pulmonary Ailments and Bronchoobstructive Syndrome The patients suffering from the indicated types of pathology were treated in much the same manner as in Example 1, except that effectiveness of treatment was checked by the use of electrocardiographic and chest roentgenographic techniques on the basis of total and biochemical blood count and urinalysis results.

The total number of patients undergoing treatment was 24. In the case of bronchial asthma and chronic obstructive bronchitis the obstructive syndrome was rapidly stopped, the breathing function improved and, in some instances, the dependence of the intensity of the pathologic process on the hormonal state was essentially eliminated.

The group of subjects included patient K aged 39. Diagnosis: bronchial asthma, infectious-allergic form, asthmaticus state. The patient had been ill for 14 years. The known treatment methods (acupuncture and electro-puncture) had not given any appreciable effect. Routine measures included the use of a broncholithic complex, hormonal preparations, intravenous infusion and inhalation. The patient suffered from daily asphyxia attacks.

Biologically active acupuncture zones chosen with due regard for cartography of zone therapy were affected with electromagnetic radiation in the wave band from 5 to 5.5 mm at a spectral power density of $10^{-16}$ to $10^{-18}$ W/Hz for 20 minutes. The clinical manifestations were characterized by disappearance of difficult aspiratory breathing, shorter inhalation, normal exhalation, fewer stertors, absence of asphyxia, a normal respiration rate, and improved cardiac rhythm. An objective analysis showed an improvement in the external respiration function.

The course of treatment involved 9 procedures. Attacks of asphyxia stopped after the second procedure, while stable normalization of the external respiration function had occurred by the 9th day, as indicated by spirograms and the Whatchal-Tiffno test. Effectiveness of treatment was checked three times during six months. The patient's condition was satisfactory.

EXAMPLE 3

Treatment of Patients Suffering from Postthyrotoxic Encephalophthalmopathy

The patients suffering from postthyrotoxic encephalophthalmopathy were treated in much the same manner as in Example 1, except that the examination involved the use of immunological and biochemical techniques.

The total number of patients undergoing treatment was 12. Effectiveness of treatment was characterized by the following manifestations occurring after 8 to 10 procedures: total absence of headaches, improved sleep, relieved eye pain, alleviated exophthalmos, increased working capacity.

The group of subjects included female patient M aged 30. Clinical examination showed that she suffered from headaches, vertigo, sharp eye pain, exophthalmos, false sensation of foreign matter in the eyes, photophobia, edematic periorbital tissue, and diplopia. Before applying for institution treatment, the patient had undergone subtotal resection of the thyroid gland in connection with toxic diffuse goiter. After the operation, there appeared and progressed the following ocular and neurologic signs: hernia of the eyeballs, edema and hyperemia of the mucous membrane of the eye, retraction of upper eyelids, asynchronous movement of the eyeballs and the upper eyelids, increased abdominal reflexes and decreased tendon reflexes, disrupted ovarian and menstrual cycles, blood pressure instability, excessive sweating. Conservative treatment proved to be inefficient.

Biologically active zones T-20, VB-1 and G1-4. were affected with electromagnetic radiation in the wave band from 5 to 5.5 mm at a spectral power density of $10^{-12}$ to $10^{-15}$ W/Hz. A single daily procedure lasted for 25 minutes. The course of treatment included 8 procedures described.

The above treatment resulted in disappearance of headaches, sharp pain in the eyes, exophthalmos and hyperemia of the mucous membrane of the eye. Also, the afore-mentioned reflexes were normalized.

The patient was subjected to clinical examination three times during six months. No complaints were recorded. The symptom-complex of postthyrotoxic encephalophthalmopathy was not observed. The ocular and neurologic signs tended to disappear one month after the treatment.

EXAMPLE 4

Treatment of Patients Suffering from Infantile Cerebral Paralysis

The proposed method was applied to patients suffering from infantile cerebral paralysis in the form of spastic diplegia. The techniques used were essentially the same as in Example 1. Subject to treatment were children whose condition was predominantly characterized by dyskinesia. The age of the children differed. Some of the causes of the derangement are the effect of unreduced topical reflexes, pathologic deviations and myogenic contracture of the upper and lower extremities, presence of pathologic reflexes and syncinesis. Some of the patients also suffered from alalia in the form of spasmodic and paretic dysarthria.

During a single action and repeated treatment procedures, all the children manifested a reduced level of bioelectric activity of spastically strained muscles and their synergistics, and also improved spectral characteristics and better reciprocal action. There occurred normalization of the vestibulometric parameters regulated primarily with respect to the mesencephalitis and cortical levels which are the highest regulation levels, said process involving elimination of interlabyrinth asymmetry and improvement of interaction between the otolithic organs and the semicircular ducts. The locomotive function was somewhat improved due to normalization of the paraclinical indices.

In the proposed method and the device therefor, effectiveness of treatment was checked by the use of global electromyography of muscles of the upper and lower extremities with analysis of the phase-amplitude characteristics during treatment and evaluation of reciprocal connections. Also used were vestibulometric techniques involving level organization, in which neurodynamic indices were predominantly normalized.

The proposed method was applied to a group of 40 patients suffering from infantile cerebral paralysis. The age of the children varied between 1 and 15 years. The group included children having moderate and severe forms of the disease and patients lacking speech contact due to young age or grave psychic distrubances.

The course of treatment involved 10 20-min procedures. If required, the treatment was repeated after a month. The proposed device was used to induce electromagnetic radiation in the wave band from 5 to 5.5 mm with a continuous spectrum therein at a spectral power density of $10^{-16}$ to $10^{-18}$ W/Hz.

The biologically active zones chosen for treatment included acupuncture points, hypersensitive or hyposensitive areas, the Zakhariin-Head zones, scalp and plantar zones, etc.

Signs of relaxation were noted after 10 to 15 seconds.

The following clinical signs were observed during treatment: reduced pathologic muscular hypertension, increased mobility of affected joints, enhanced strength of paretic muscles, improved motor activity, fewer and less pronounced unintentional movements, better coordination of movements, improved posture. Furthermore, the patients manifested a more adequate response to external stimulus, normal sleep and appetite, a wider choice of words, and more distinct speech. Due to lesser fatiguability, the children were able to cover distances several times as great as those before treatment.

EXAMPLE 5

Treatment of Patients Suffering from Chronic Alcoholism, Manic-depressive Psychosis, Various Forms of Neuroses and Tabacism The method was accomplished essentially in the same manner as in Example 1.

Patient D aged 42 has been a habitual drunkard since the age of 24. At the age of 15 there appeared the first signs of abstinence adversely affecting the patient's working capacity. He had been repeatedly treated at narcological institutions. After treatment, the patient was still addicted to liquor and the ensued remission attributable to fear did not last for more than six months. During the period immediately preceding microwave resonance therapy, the manner of drinking had undergone a change, more specifically, fits of hard drinking lasting for 5 to 7 days were followed by abstention periods up to one month. The patient was delivered to the institution when his booze-up was in full swing. Diagnoses: second stage of chronic alcoholism, abstinence syndrome.

Use was made of electromagnetic radiation in the wave band from 4.8 to 5.5 mm at a spectral power density of $10^{-12}$ to $10^{-18}$ W/Hz. The duration of a single procedure was 15 to 25 minutes. The affected biologically active points were ZU-LI-PANG, auricular lung point P23 and HE-GU. The ZU-LI-PANG point was affected during the first four procedures, while said auricular lung point P23 was affected in the course of the next five procedures from the 5th to the 9th. Thereafter, with the patient exhibiting indifference to alcohol, electromagnetic radiation was applied to the HE-GU point. The entire course involved 14 procedures.

When the last procedure was used, the patient developed aversion to alcoholic smell accompanied by somatic and vegetative reactions.

The results obtained in treatment of patients suffering from chronic alcoholism were as follows. In a group of 28 subjects 18 patients had therapeutic remission over six months, 2 patients had therapeutic remission over one year, and 3 patients showed no clinical effect. Effectiveness of treatment was checked by clinical methods.

The treatment manic-depressive psychosis produced an appreciable clinical effect involving restoration of working capacity.

As a result of treatment, the patients suffering from chronic alcoholism and tabacism had longer abstention periods.

Neurotic therapy produced a clinical effect in 60% of patients out of a group of 13 subjects.

The treatment of tabacism produced a curative effect in 75% of cases.

What is claimed is:

1. A method of microwave resonance therapy consisting in treating predetermined biologically active zones of a patient with a continuous frequency spectrum low-intensity EHF electromagnetic radiation of a spectral power density from $10^{-16}$ W/Hz to a value approaching a quantum limit in a therapeutical effective frequency region, each application lasting from 15 to 30 minutes.

2. A method as claimed in claim 1, wherein the spectral power density of the electromagnetic radiation is in the range of $10^{-16}$ to $10^{-18}$ W/Hz.

3. A method as claimed in claim 1, wherein a patient is treated for infantile cerebral paralysis, by up to 10 applications which are effected each for a period of time up to 20 minutes to biologically active zones of the patient with electromagnetic radiation in the wave band from 1 to 6 mm of a spectral power density from $10^{-16}$ to $10^{-18}$ W/Hz.

4. A device for microwave resonance therapy comprising: an electromagnetic EHF radiation source having an output for generating a continuous frequency spectrum low-intensity EHF electromagnetic radiation of a spectral power density from $10^{-16}$ W/Hz to a value approaching a quantum limit; and a radiating antenna having an input connected to the output of the electromagnetic EHF radiation source.

5. A device as claimed in claim 4, wherein the electromagnetic EHF radiation source is adapted for generating a continuous frequency spectrum low-intensity EHF electromagnetic radiation of a spectral power density from $10^{-16}$ to $10^{-18}$ W/Hz.

6. A device as claimed in claim 4, wherein the electromagnetic EHF radiation source comprises a noise generator.

7. A device as claimed in claim 6, wherein the noise generator comprises:
- a supply voltage generating means having an output;
- an active element for emitting an electromagnetic energy having an input connected to the output of the supply voltage generating means, and having an output;
- means for channeling electromagnetic energy emitted by the active element, said means having an input connected to the output of the active element, and said means having an output connected to the input of the radiating antenna.

8. A device as claimed in claim 7, wherein the means for channeling electromagnetic energy is a waveguide adapted to pass high frequencies of electromagnetic energy.

9. A device as claimed in claim 8, further comprising a waveguide transformer interconnecting the means for channeling electromagnetic energy and the radiating antenna.

* * * * *